(12) United States Patent
He et al.

(10) Patent No.: US 8,418,526 B2
(45) Date of Patent: Apr. 16, 2013

(54) SYSTEM AND METHOD FOR TESTING GAS MIGRATION PROCESS IN COAL-ROCK MASS

(75) Inventors: Manchao He, Beijing (CN);
Chunguang Wang, Beijing (CN);
Haijiang Zhang, Beijing (CN); Dejian Li, Beijing (CN)

(73) Assignee: China University of Mining & Technology ( Beijing), Beijing (CN)

( * ) Notice: Subject to any disclaimer, the term of this patent is extended or adjusted under 35 U.S.C. 154(b) by 0 days.

(21) Appl. No.: 13/386,050

(22) PCT Filed: Jul. 15, 2010

(86) PCT No.: PCT/CN2010/001065
§ 371 (c)(1),
(2), (4) Date: Jan. 20, 2012

(87) PCT Pub. No.: WO2011/009287
PCT Pub. Date: Jan. 27, 2011

(65) Prior Publication Data
US 2012/0118041 A1    May 17, 2012

(30) Foreign Application Priority Data
Jul. 20, 2009    (CN) .......................... 2009 1 0088810

(51) Int. Cl.
*G01N 7/00*    (2006.01)
(52) U.S. Cl.
USPC ........................................................ 73/19.01
(58) Field of Classification Search ................. 73/19.01, 73/19.02, 19.04, 19.05, 19.09, 23.2
See application file for complete search history.

(56) References Cited

U.S. PATENT DOCUMENTS

| | | | | |
|---|---|---|---|---|
| 4,459,103 A | * | 7/1984 | Gieskieng | 432/43 |
| 2006/0265954 A1 | * | 11/2006 | Dogru et al. | 48/197 R |
| 2009/0260416 A1 | * | 10/2009 | Coleman et al. | 73/19.01 |

FOREIGN PATENT DOCUMENTS

| | | | |
|---|---|---|---|
| CN | 1117113 A | | 2/1996 |
| CN | 101034050 A | | 9/2007 |
| CN | 201016909 Y | | 2/2008 |
| CN | 101216405 A | | 7/2008 |
| JP | 2001113116 A | * | 4/2001 |

OTHER PUBLICATIONS

Machine Translation, Tang, Jupeng, Theoretical and Experimental Research of Storage of Coalbed Methane by NMRI Technique, Univ Liaoning Technology, Ph.D. Thesis, Dec. 30, 2006, pp. 47-72.*
Machine Translation, Hirose et al., JP 2001-113116, Apr. 24, 2001.*

(Continued)

*Primary Examiner* — Hezron E Williams
*Assistant Examiner* — David Z Huang
(74) *Attorney, Agent, or Firm* — Renner, Otto, Boisselle & Sklar, LLP

(57) ABSTRACT

A system and method for testing gas migration process in the coal and rock mass are disclosed. The method includes the following steps: selecting a cylindrical coal sample, applying an axial pressure and a radial pressure to the coal sample under a sealing state, and/or increasing temperature, to desorb gas absorbed by the coal sample; guiding the gas desorbed from the coal sample by a guiding passage, detecting gas flow rate and pressure, analyzing gas composition and content, and achieving a data statistics. The method provides a theory and data basis for researching the forming and occurring process of gas outburst accident in coal mine. The system is simple and easy to use, and is suitable for migration research of the gas absorbed in the deep coal-rock mass.

5 Claims, 3 Drawing Sheets

OTHER PUBLICATIONS

Tang, Jupeng, Theoretical and Experimental Research of Storage and Transport of coalbed Methane by NMRI Technique, Univ Liaoning Eng Technology, Ph.D Thesis, Dec. 30, 2006, pp. 54●57.

International Search Report, Application No. PCT/CN2010/001065, mailed Oct. 21, 2010.

Tang, Jupeng, Theoretical and Experimental Research of Storage and Transport of coalbed Methane by NMRI Technique, Univ Liaoning Eng Technology, Ph.D. Thesis, Dec. 30, 2006, pp. 54-57. (previously submitted in Information Disclosure Statement of February 3, 2012, partial English Translation being provided herein).

* cited by examiner

SYSTEM AND METHOD FOR TESTING GAS MIGRATION PROCESS IN COAL-ROCK MASS

CROSS REFERENCE TO RELATED APPLICATIONS

This application is a national phase entry of International Application No. PCT/CN2010/001065 filed Jul. 15, 2010, which claims priority of Chinese Application No. CN200910088810.6 filed on Jul. 20, 2009, the contents of which are hereby incorporated by reference.

TECHNICAL FIELD

The invention relates to mining safety engineering art, and more particularly to a system and method for testing gas migration process in coal-rock mass.

BACKGROUND ART

Coal is a kind of complex porous medium, in pore structure of which a lot of methane and carbon dioxide gas are absorbed. As the exploration of coal resource is performed towards deep coal seam, low-gas mine gradually turns into high-gas mine, and the absorbed gas is desorbed to be in free-state with the increment of environment temperature and the decrement of stress, and migrates in the pore structure of the coal. During the exploration and excavation in deep coal-rock mass, although the free-state gas may go out of roadways upon the ventilation of the mine, much gas is still absorbed in the coal-rock mass, which becomes one factor that causes various gas accidents. As a result, research on desorption and migration characteristics of the absorbed gas occurring in the coal seam is a technical difficulty in the mining safety engineering, and is also an urgent problem that needs to be solved.

Currently, the vast majority of researches on the desorption-migration process of the gas absorbed in the coal-rock mass focus on the amount of absorbed gas and desorbed gas in different temperature and pressure conditions, whereby the absorbing-desorbing ability of the tested coal sample is evaluated. The process of the conventional research will be described below: first, performing a vacuum degassing to the collected coal sample; then injecting air with a certain pressure to make the coal sample achieve absorption saturation; thereafter, performing a pressure relief and desorption process, and detecting the desorbed gas with instruments such as a flow meter, a pressure meter or the like to accomplish the experiment process. In the above-mentioned process, although a maximum adsorption gas amount of the coal sample and the Langmuir adsorption constant under isothermal condition can be obtained, it cannot reflect migration regulation of the gas absorbed in the coal seam in multiple physical fields, such as a temperature field, a stress field and a seepage field, before and after the exploration, and also cannot realistically simulate the absorbing-desorbing process of the gas in the coal-rock mass under real environment in deed. As a result, experiment data will be lack of reliability to some extent, such that it fails to provide a basis for accurately determining the forming time and reason of gas outburst, and may generate a potential danger for safety production.

SUMMARY OF THE INVENTION

The object of the present invention is to provide a system and method for testing gas migration process in coal-rock mass, which is used to research the migration regulation of the gas absorbed in deep coal-rock mass so as to overcome the existing problems in the prior art, for example, in the prior art the absorption-desorption process of the coal-rock mass under real environment cannot be realistically simulated, the experiment data are lack of reliability, and the basis for accurately determining the forming time and reason of gas outburst cannot be provided.

To achieve the above object, the invention provides a method for testing migration process of gas in coal-rock mass, comprising steps of: selecting a cylindrical coal sample; applying an axial pressure, a radial pressure or a warm-up temperature control or any combination thereof to the coal sample under sealing state, for desorbing the gas absorbed in the coal sample; and guiding the gas desorbed from the coal sample via a guiding passage, detecting flow rate and pressure of the gas, as well as analyzing composition (ingredient) and content of the gas to accomplish data statistics.

According to a preferred embodiment of the method, the coal sample may be directly extracted from its original state.

According to a preferred embodiment of the method, a radial pressure may be applied to the coal sample by a hydraulic method, and an isolating layer may be covered on a surface of the coal sample to prevent hydraulic liquid from permeating through the coal sample.

According to a preferred embodiment of the method, the guiding passage is disposed along an axial direction of the coal sample.

To achieve the object of the invention, the invention provides a system for testing gas migration process in coal-rock mass, comprising: a loading system, for applying an axial pressure and/or a radial pressure to a coal sample under sealing state such that the gas absorbed in the coal sample is desorbed; a temperature control system, for controlling a temperature of the coal sample under the sealing state such that the gas absorbed in the coal sample is desorbed; a gas composition detecting and measuring system, for detecting pressure, composition, flow rate and content of each composition of the gas desorbed from the coal sample; and a data acquisition instrument, for collecting data outputted from the gas composition detecting and measuring system as well as analyzing, comparing and summarizing the outputted data; wherein the gas composition detecting and measuring system is connected to the loading system via a guiding passage, and the data acquisition instrument is electrically connected to the gas composition detecting and measuring system.

According to a preferred embodiment of the system, the loading system may be a triaxial cell that comprises a sealing chamber, provided with an inlet and an outlet; an oil cylinder, disposed outside the sealing chamber and with a cylinder rod protruding into the sealing chamber vertically; and two axial pressure heads, located in the sealing chamber and connected to an end of the cylinder rod and a base of the sealing chamber, respectively; the cylinder rod and the axial pressure heads connected thereto being provided with guiding tubes which communicate with each other and form a part of the guiding passage.

According to a preferred embodiment of the system, the temperature control system may comprise: a temperature controller, including a detecting head for contacting with a surface of the coal sample and detecting the temperature of the coal sample; and a heater, controlled by the temperature controller, and disposed in the loading system to heat the coal sample.

According to a preferred embodiment of the system, the gas composition detecting and measuring system may comprise: a pressure meter; and a pressure solenoid valve, a flow meter and a gas chromatograph sequentially connected, wherein the pressure meter may be connected to the guiding passage and the pressure solenoid valve.

According to a preferred embodiment of the system, two flow meters are provided, and the two flow meters are connected in parallel between two switches, respectively, and the two switches are selected depending on gas flow rate to match flow meters with different measuring ranges for ensuring the measuring precision.

The invention is directed to study the original absorbed gas occurred in the coal. A pressure loading experiment is preformed on an original coal sample by means of axial pressure and radial confining pressure, and the temperature of the coal sample is controlled, so as to realistically simulate a process of the absorbed gas transforming from an absorption state to a free state and from a diffusion state to a seepage state when the coal-rock mass is explored and damaged during the practical exploring process, as a function of the variation in temperature and stress. Thus, the detected data of pressure, flow rate, composition and content of the desorbed gas will be accurate and reliable, so that a convincing theory and data basis could be provided for researching the forming and occurring process of gas outburst accident in the coal mine. The invention has a skillful and reasonable concept and a realistic simulating process, so that it can fully reproduce desorption, migration and diffusion process of the absorbed gas during the coal rupture process. The invention is quite suitable for researching the migration of gas absorbed in deep coal-rock mass.

DETAILED DESCRIPTION OF THE PREFERRED EMBODIMENTS

Figure 1:
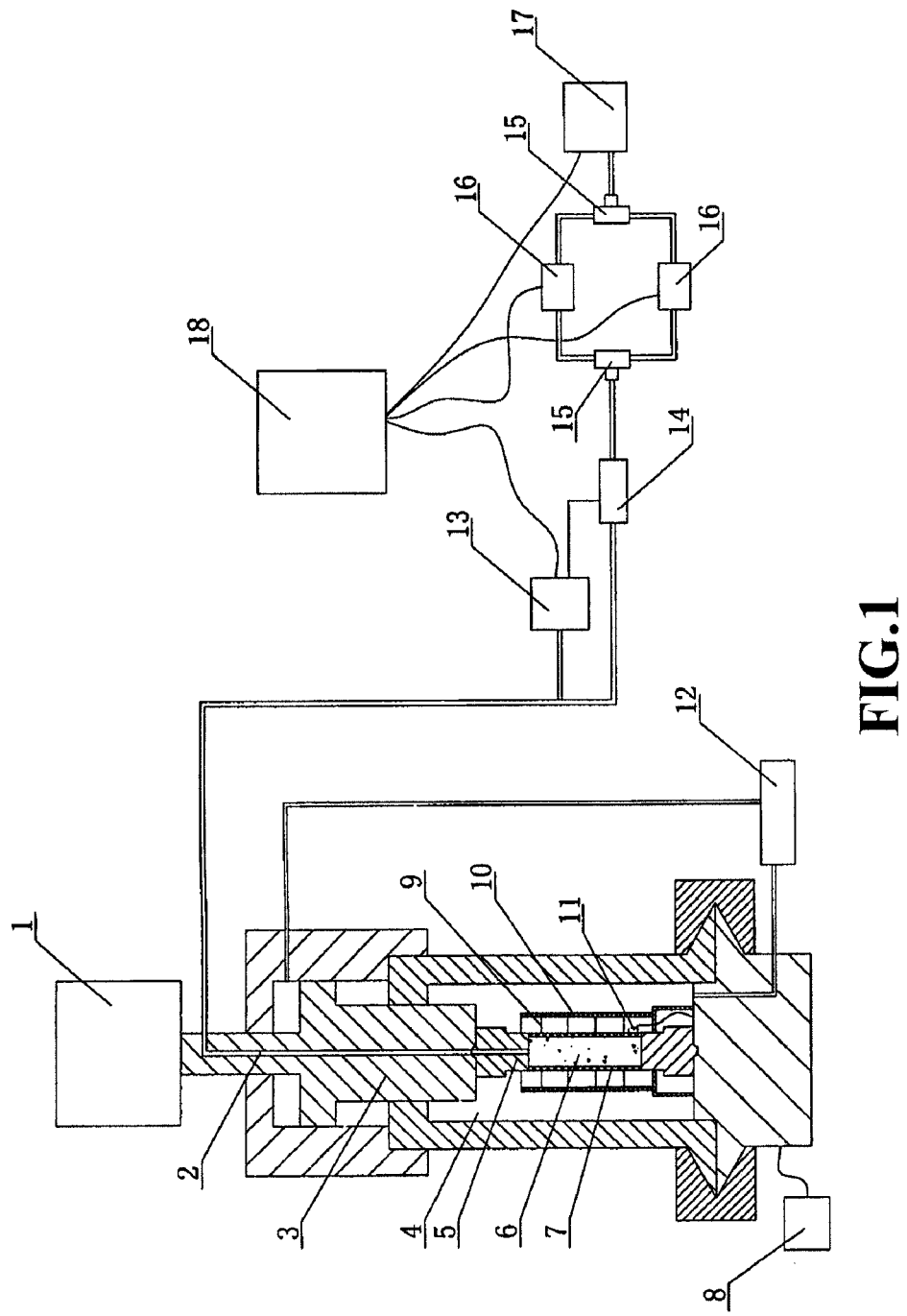
FIG. 1 is a schematic diagram showing a structure of a system for detecting gas migration process in coal-rock mass according to a first preferred embodiment of the invention.

As illustrated above, the invention has the following objects: under multiple physical fields, realistically simulating migration process of the gas absorbed in coal-rock mass after the coal-rock mass is damaged by stress; detecting pressure and flow rate of the migrating gas as well as content of each composition of the migrating gas; providing an accurate and reliable experiment basis for researching gas accidents in coal mine roadways, and providing an estimation basis for preventing from such gas accidents.

In a preferred embodiment of the invention, the method for testing gas migration process in coal-rock mass includes steps as below:

First, a cylinder coal sample is selected and fixed under sealing state, the coal sample is applied an axial pressure and a radial pressure and is subjected to a warm-up temperature control, such that the gas absorbed in the coal sample is desorbed.

The coal sample is selected in its original state and is directly used thereafter, so that affection and damage on the absorbed gas resulting from man-induced factors can be reduced as much as possible. The coal sample is in a shape of cylinder. The sampling process of the cylindrical coal sample is simple, and a radial force can be applied to the cylindrical coal sample in a uniform, reliable and convenient manner.

The experiment process under the sealing state can ensure that the axial and radial pressure experiments and the warm-up temperature control can be conducted quantifiably in a controlled manner, such that a process of the absorbed gas transforming from an absorbed state to a free state and migrating in the coal sample can be realistically reproduced under multiple physical fields, so as to ensure accuracy and reliability of the experiment process and data. Naturally, in the experiment process of coal sample under the sealing state, only one of the axial pressure, the radial pressure and the warm-up temperature control or even any combination thereof can also be conducted, so as to detect the affection on the migration process of the gas absorbed in the coal sample in different conditions.

The axial pressure and the radial pressure can be applied by a mechanical transmission method.

The radial pressure can be applied by a hydraulic method, in which the hydraulic force is uniform and stable, and has a large pressure and a reliable performance. To avoid liquid used in a hydraulic transmission method from permeating into the coal sample to affect and damage the experiment process, during the fixation of the coal sample, an isolation layer can be covered on a surface of the coal sample, so as to completely isolate the coal sample and the liquid and ensure the uniform transfer of the pressure.

The warm-up temperature control can directly rise the temperature of the coal sample, or the temperature of the whole sealing environment, as long as such temperature control process can precisely reflect the temperature of the coal sample.

The sealing state during the experiment can be achieved by a sealing chamber that can be subjected to a certain pressure, and the whole experiment process shall be performed under the sealing state.

Next, a guiding passage is used to guide the desorbed gas from the coal sample, and the flow rate and pressure of the gas are detected, the gas composition and gas content are analyzed to achieve data statistics.

The gas desorbed from the coal sample is guided out under the sealing state; the desorbed gas is detected by means of a pressure meter, a flow meter and a gas chromatograph, thereby obtaining the pressure and flow rate of the gas, as well as the composition and content of the gas; and a relative graph can be obtained after summarizing the detected data. With the graph, the researcher can directly understand the flow rate and migration condition of the gas desorbed from coal-rock mass as a function of the variation in pressure and temperature, and can obtain the desorption process of the gas absorbed in the coal sample in various states and periods, thereby providing theory basis for avoiding and preventing gas accidents.

The guiding passage needs to be sealed well, and shall guide the gas desorbed from the coal sample smoothly. The coal sample needs to bear the radial pressure evenly in the experiment. Therefore, in order to decrease the affection on the coal sample caused by the guiding passage, the guiding passage shall be disposed along an axial direction of the coal sample. The axial guiding passage is easy to be manufactured and used, and can also reduce the affection on the loading pressure of the coal sample.

To obtain a certain pressure of the escaped gas and realistically simulate the migration process of the gas after the coal sample is damaged by stress, a pressure control switch may be disposed between the pressure meter and the flow meter. The pressure control switch opens the gas guiding tube of the flow meter after the pressure meets a certain condition, such that the gas desorbed from the coal sample has an ejection process during migration. In view of the limitation of the measuring range and accuracy requirement of the flow meter, the gas guiding tube can be connected to a plurality of flow meters with different measuring ranges at a time in order to facilitate the detection in different conditions.

Hereinafter, a preferred embodiment of the system for testing gas migration process of in coal-rock mass will be described with reference to FIG. 1.

In a preferred embodiment as shown in FIG. 1, the system includes: a loading system for applying an axial pressure and a radial pressure to a coal sample 6 under sealing state so as to make the gas absorbed in the coal sample 6 to be desorbed; a temperature control system for controlling the temperature of the coal sample 6 under the sealing state; and a gas composition detecting and measuring system for detecting composition and flow rate of the gas desorbed from the coal sample 6 and content of each composition of the gas. In the preferred embodiment, the system also includes a data acquisition instrument 18 for collecting data outputted from the gas composition detecting and measuring system, as well as analyzing, comparing and summarizing the outputted data. The gas composition detecting and measuring system is connected to the loading system via a guiding passage 2, and the data acquisition instrument 18 is electrically connected to the gas composition detecting and measuring system. The gas composition detecting and measuring system makes a quantitative analysis of the desorbed gas and completely obtains the relative data such as the composition, content, pressure etc. of the desorbed gas, and the data acquisition instrument 18 summarizes and compares the relative data and forms associated data graphs.

In the preferred embodiment, the loading system is a triaxial cell, which includes a sealing chamber 4, an oil cylinder 1 and two axial pressure heads 5 located in the sealing chamber 4. The sealing chamber 4 is provided with an oil inlet and an oil outlet. Pressure oil can be injected into the sealing chamber 4 through an external oil pump 12, to form an environment with uniform pressure within the sealing chamber 4. To prevent the pressure oil from contacting with a surface of the coal sample 6, an isolation layer 7 is sleeved on the surface of the coal sample 6. The oil cylinder 1 is fixed at the top of the sealing chamber 4, and a cylinder rod 3 protrudes into the sealing chamber 4 perpendicularly. One of the two axial pressure head 5 is connected to an end of the cylinder rod 3, and the other is located at a base within the sealing chamber 4. An end face of axial pressure head 5 is provided with a protrusion, while the end of the cylinder rod 3 and the base of the sealing chamber 4 are provided with recesses in cooperation with the protrusions. The protrusions of the two axial pressure heads 5 are embedded in the recess at the end of the cylinder rod 3 and the recess on the bottom surface of the sealing chamber 4, respectively. There is a guiding passage 2 runs through the cylinder rod 3 and the axial pressure heads 5 connected thereto, and an outlet of the guiding passage 2 in the cylinder rod 3 leads to outside of the sealing chamber 4.

The temperature control system includes a temperature controller 8 and a heater 10. The heater 10 is a tubular insulator bobbin, on which a ceramic-insulated resistance wire 9 is coiled; and the heater 10 is fixed in the sealing chamber 4 and sleeved around the coal sample 6 to be experimented. The temperature controller 8 is installed outside of the sealing chamber 4, and is connected to the heater 10 via a wire. A detecting head 11 on the temperature controller 8 contacts with the surface of the coal sample 6 within the sealing chamber 4.

The gas composition detecting and measuring system includes a pressure meter 13, a pressure solenoid valve 14, two flow meters 16, two hand switches 15 and a gas chromatograph 17. The pressure meter 13 is connected to a piping at the outlet of the guiding passage 2, and the pressure solenoid valve 14 is connected to the pressure meter 13 and the flow meters 16. The pressure solenoid valve 14 is in a normally closed state. When a certain pressure is reached, the pressure solenoid valve 14 will be opened. The hand switch 15 is a two-position three-way valve. To ensure the accuracy and safety in measuring the flow rate, the two flow meters 16 are connected in parallel with each other. The measuring ranges of the two flow meters 16 are different, so they can measure different gas flow rates. Each of the two two-position three-way valves control whether to communicate the corresponding one of the two flow meters 16 and the gas chromatograph 17, respectively; and the data detection of the desorbed gas can be accomplished by means of the flow meters 16 and the gas chromatograph 17.

The data acquisition instrument 18 is electrically connected to the pressure meter 13, the flow meters 16 and the gas chromatograph 17, respectively. The data acquisition instrument 18 collects and processes the data to form a graph showing the relationship between the detected data and time.

During the experiment of the migration process of gas absorbed in coal-rock mass in the preferred embodiment in FIG. 1, the cylindrical coal sample 6 is sleeved by an isolation layer 7 which may be in a form of a fluorine rubber sleeve. Both ends of the coal sample 6 abut against the two axial pressure heads 5, respectively; and both ends of the fluorine rubber sleeve are connected and sealed to surfaces of the axial pressure heads 5 with silica gel. It ensures that the surface of the coal sample 6 cannot contact with external hydraulic oil. The cylinder rod 3 is moved such that the recesses in the cylinder rod 3 and the base of the sealing chamber 4 receive the protrusions of the two axial pressure heads 5. The heater 10 is sleeved to the coal sample 6, and the bottom of the heater 10 is fixed to the bottom of the sealing chamber 4. The detecting head 11 is fixed within the sealing chamber 4 and contacts with the fluorine rubber sleeve on the surface of the coal sample 6. The sealing chamber 4 is closed and the hydraulic oil is injected into the sealing chamber 4 from the external oil pump 12, such that the sealing chamber 4 is filled with oil. The coal sample 6 maintains a vertical state within the sealing chamber 4, and the coal sample 6, the heater 10 and the detecting head 11 are completely immersed into the pressure oil. The top of the coal sample 6 communicates with the external pressure meter 13, the flow meter 16 and the gas chromatograph 17 via the cylinder rod 3 and the guiding passage 2 in the axial pressure head 5 connected to the cylinder rod.

In the experiment, a heating temperature can be set. The operation of the heater 10 is controlled by the temperature controller 8 such that the coal sample 6 reaches a desired temperature. The oil cylinder 1 pushes the cylinder rod 3 to apply the axial pressure to the coal sample 6 within the sealing chamber 4. Meanwhile, the hydraulic oil in the sealing chamber 4 generates a confining pressure to the coal sample 6. The confining pressure is applied to the side surface of the coal sample 6 evenly. Under temperature field and stress field, the gas absorbed in the coal sample 6 is desorbed and migrates, the escaped gas flows out of the sealing chamber 4 via the guiding passage 2 from the end of the coal sample 6. The pressure meter 13 detects the pressure of the escaped gas at any time. Since the pressure solenoid valve 14 is in a normally closed state, the desorbed gas in the guiding passage 2 will not directly enter into the passage of the flow meter 16. Instead, the pressure solenoid valve 14 will be opened when the pressure reaches a certain value as the increasing of the desorbed gas. According to the flow rate of the desorbed gas, the two two-position three-way valves are operated to communicate with the corresponding flow meter 16 and the gas chromatograph 17. The flow meters 16 and the gas chromatograph 17 detect the flow rate, composition and content of the gas. Then, the data acquisition instrument 18 summarizes the detected data and draws a graph representing desorption and migration of the gas absorbed in the coal sample 6 in various times, various periods and different pressures.

In the preferred embodiment, a sealing environment is provided for the originally extracted coal sample by means of the triaxial cell; the migration of the gas in deep coal-rock mass under multiple physical fields in real environment can be simulated by changing the temperature and pressure within the sealing chamber; and the relative data about the desorbed gas can be detected and obtained by means of the pressure meter, the flow meter and the gas chromatograph. The whole system can perform a real and effective simulating process in a simple and convenient manner. Moreover, the collecting and measuring of data can be achieved precisely and reliably.

Consequently, the preferred embodiment shown in FIG. 1 can simulate the forming and occurring process of outburst of mine gas absorbed in deep coal-rock mass in various environment conditions, and thus provide theory and data basis for preventing from gas accidents.

Figure 2:
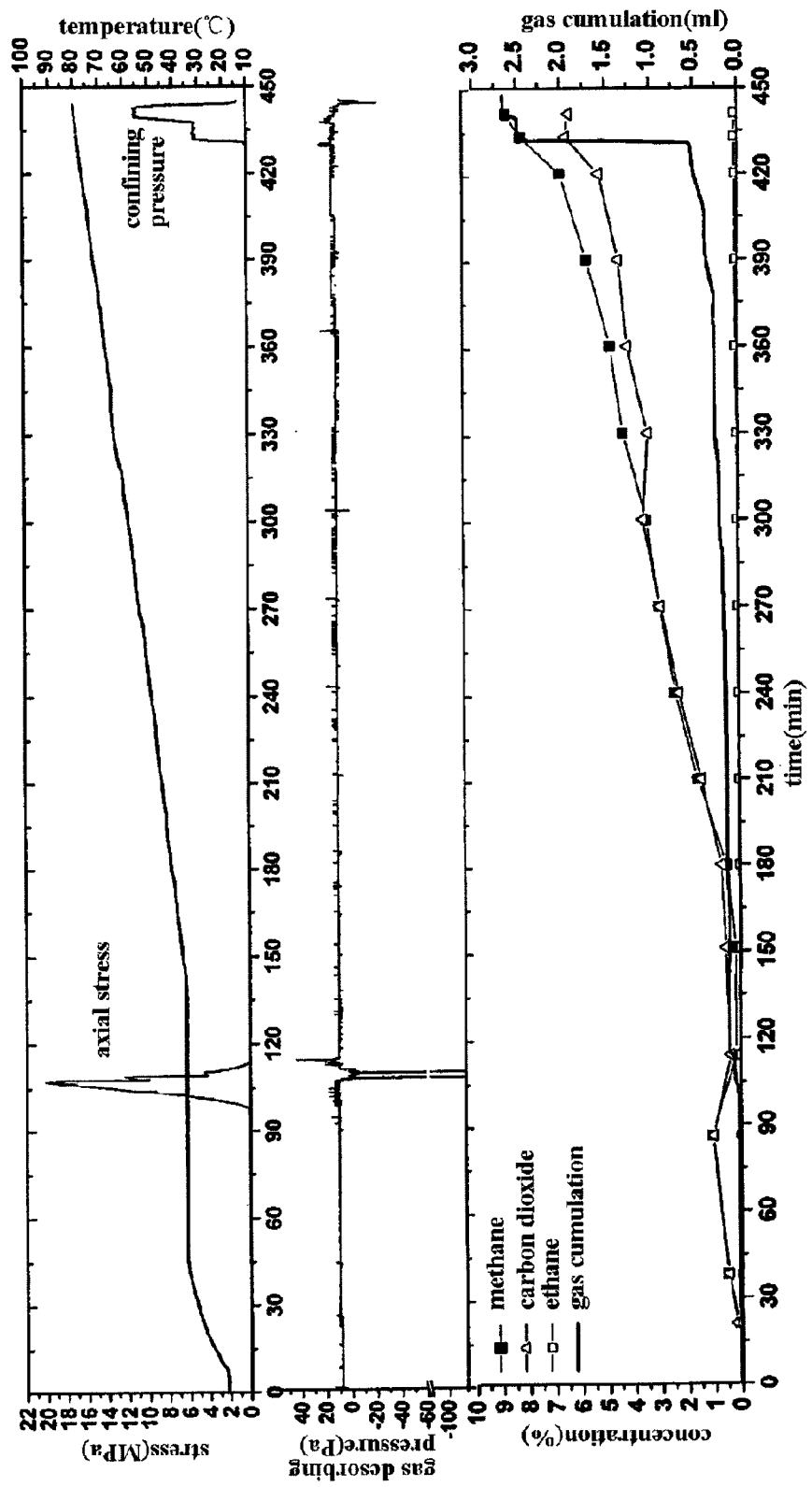
FIG. 2 shows a desorption process of the gas absorbed in coal under the effect of temperature and pressure.

FIG. 2 shows a graph of the desorption and migration process of the gas absorbed in the coal sample under the effect of temperature and pressure. After the coal sample is damaged by the axial pressure, the escaped pressure of gas decreases sharply to become a negative value, and then comes back to a normal pressure after a period of time. After the coal sample is broken, the permeability thereof increases, and the concentration of each kind of gas increases correspondingly as the increasing of temperature. When the temperature reaches 70° C., a side pressure is applied to the coal sample such that the pressure of the gas increases. Thus, a lot of gas will escape from the coal sample, and the concentration of each composition of gas will continue to increase. It can be seen from the result of the experiment that new gaps generated in the coal sample under uniaxial pressure will prompt the gas to flow back, which is demonstrated by pressure decrease of gas. The confining pressure may reduce the volume of the gap, and desorb a lot of free-state gas.

Figure 3:
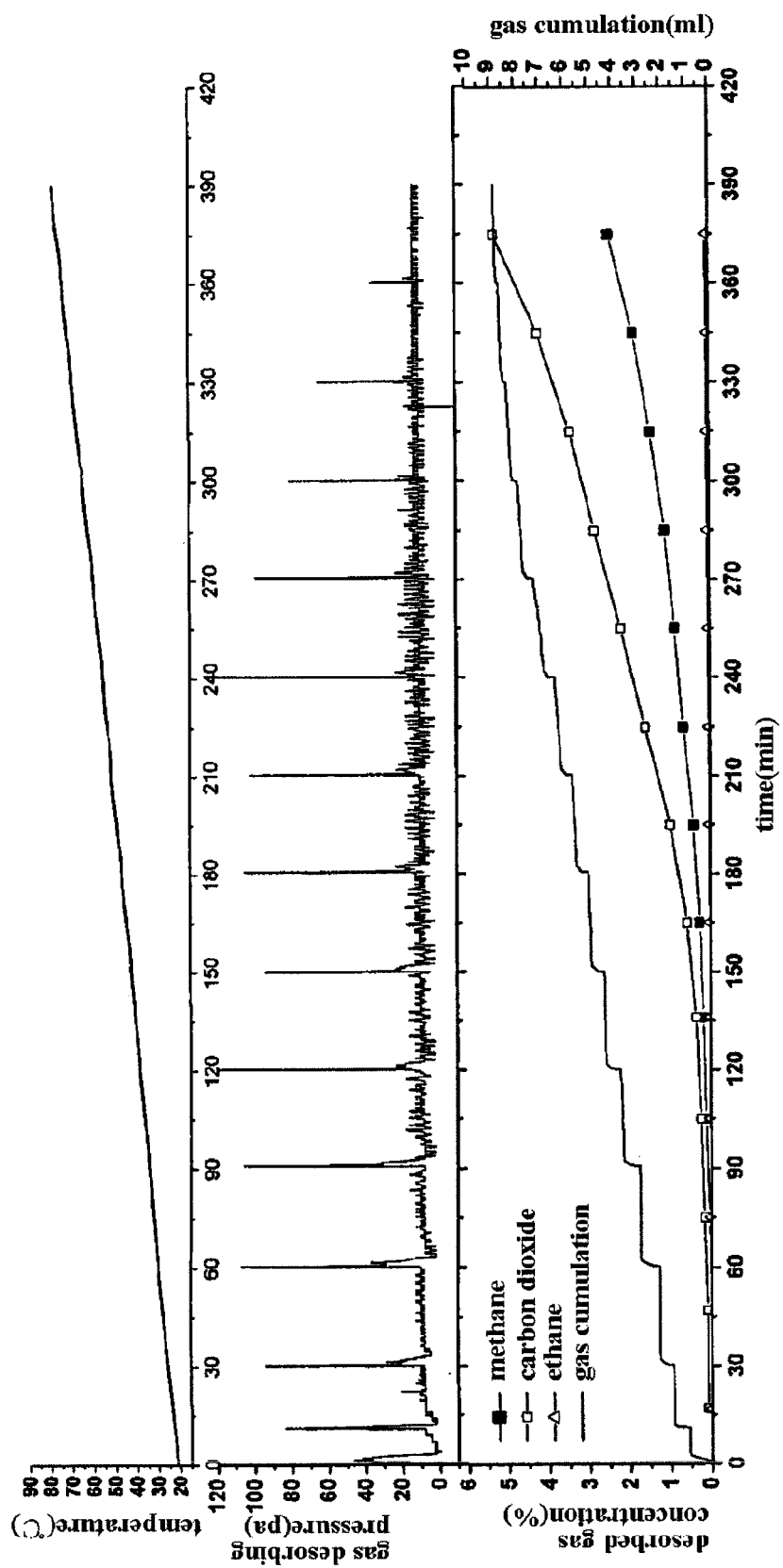
FIG. 3 shows a desorption process of the gas absorbed in coal under the effect of temperature.

FIG. 3 shows a graph of the desorption regulation of the gas absorbed in the coal under the effect of temperature. As the temperature rises linearly, the free-state gas in the coal sample is expanded to flow towards external environment. The absorbed gas is desorbed to be in a free state and diffuses towards external environment, which is demonstrated by gradually increasing of concentration of each composition of gas. It can be seen from the result of the experiment that the absorbing ability of the coal sample will be reduced under the effect of temperature. It prompts the absorbed gas to desorb into a free state and escape to external environment.

Although the invention has been described as above with reference to some preferred embodiments, it shall be noted that these preferred embodiments are not used to restrict the patent protection scope of the invention. Therefore, it shall be construed that aims to cover all the equivalent modifications or variations falling within the protection scope defined by the appended claims.

What is claimed is:

1. A system for testing gas migration process in coal-rock mass, comprising:
   a loading system, for applying an axial pressure and/or a radial pressure to a coal sample under sealing state so as to desorb the gas absorbed in the coal sample;
   a temperature control system, for controlling a temperature of the coal sample under the sealing state so as to desorb the gas absorbed in the coal sample;
   a gas composition detecting and measuring system, for detecting pressure, composition, flow rate and content of each composition of the gas desorbed from the coal sample; and
   a data acquisition instrument, for collecting data outputted from the gas composition detecting and measuring system, as well as analyzing, comparing and summarizing the outputted data;
   wherein the gas composition detecting and measuring system is connected to the loading system via a guiding passage, and the data acquisition instrument is electrically connected to the gas composition detecting and measuring system.

2. The system according to claim 1, wherein the loading system is a triaxial cell comprising: a sealing chamber, provided with an inlet and an outlet; an oil cylinder, disposed outside the sealing chamber and with a cylinder rod protruding into the sealing chamber vertically; and two axial pressure heads, located in the sealing chamber and connected to an end of the cylinder rod and a base of the sealing chamber, respectively, and the cylinder rod and the axial pressure heads connected thereto being provided with guiding tubes which communicate with each other and form a part of the guiding passage.

3. The system according to claim 1, wherein the temperature control system comprises: a temperature controller, including a detecting head for contacting with a surface of the coal sample and detecting the temperature of the coal sample; and a heater controlled by the temperature controller, the heater being disposed in the loading system to heat the coal sample.

4. The system according to claim 1, wherein the gas composition detecting and measuring system comprises a pressure meter, as well as a pressure solenoid valve, a flow meter and a gas chromatograph sequentially connected, the pressure meter being connected to the guiding passage and the pressure solenoid valve.

5. The system according to claim 4, wherein two flow meters are provided, and the two flow meters are connected in parallel between two switches, and the two switches are selected depending on gas flow rate of the gas to match flow meters with different measuring ranges for ensuring the measuring precision.

* * * * *